United States Patent [19]

Sprecker et al.

[11] Patent Number: 5,372,995
[45] Date of Patent: Dec. 13, 1994

[54] REDUCED REACTION PRODUCT OF PROTONIC ACID CATALYZED REACTION OF METHYL ETHYL KETONE AND BENZALDEHYDE AND PERFUME USES THEREOF

[75] Inventors: Mark A. Sprecker, Sea Bright; Richard A. Weiss, Pine Brook, both of N.J.; Marie R. Hanna, Keyport, N.Y.

[73] Assignee: International Flavors & Fragrances Inc., New York, N.Y.

[21] Appl. No.: 228,370

[22] Filed: Apr. 15, 1994

[51] Int. Cl.$^5$ .............................................. A61K 7/46
[52] U.S. Cl. .................................. 512/20; 512/21; 512/22; 568/313; 568/317; 568/814; 568/822; 568/308; 568/715
[58] Field of Search ................ 512/20, 21, 22; 568/313, 317, 814, 822, 308, 715

[56] References Cited

U.S. PATENT DOCUMENTS

| | | | |
|---|---|---|---|
| 3,668,255 | 6/1972 | Meuly et al. | 260/586 R |
| 4,005,147 | 1/1977 | Fischer et al. | 568/313 |
| 4,036,774 | 7/1977 | van Ouwerkerk et al. | 512/21 |
| 4,169,109 | 9/1979 | Yoshida et al. | 568/313 |
| 5,300,654 | 4/1994 | Nakajima et al. | 568/313 |

FOREIGN PATENT DOCUMENTS 604716 9/1978 Switzerland ................ A61K 7/46

OTHER PUBLICATIONS

Alder, et al, Chem. Abstracts vol. 49:5394e.
Chmielarz, et al, Tluszcze, Srodki, Piorace, Kosmet, 1975, 19(3), pp. 109–118, abstracted at Chem. Abstracts vol. 83:147254h.

*Primary Examiner*—James H. Reamer
*Attorney, Agent, or Firm*—Arthur L. Liberman

[57] ABSTRACT

Described is a two-step process for producing phenyl- and cyclohexyl-substituted oxybutane derivative-containing mixtures of our invention by means of first reacting methyl ethyl ketone with benzaldehyde in the presence of a sulfonic acid catalyst to produce a mixture of phenyl pentenone derivatives; and then hydrogenating the resulting mixture of phenyl pentenone derivatives in the presence of a hydrogenation catalyst, as well as the product produced thereby; and perfumery uses thereof for augmenting, enhancing or imparting aromas in or to perfume compositions, colognes and perfumed articles.

20 Claims, 5 Drawing Sheets

GC MASS SPECTRUM FOR EXAMPLE I. CAPILLARY

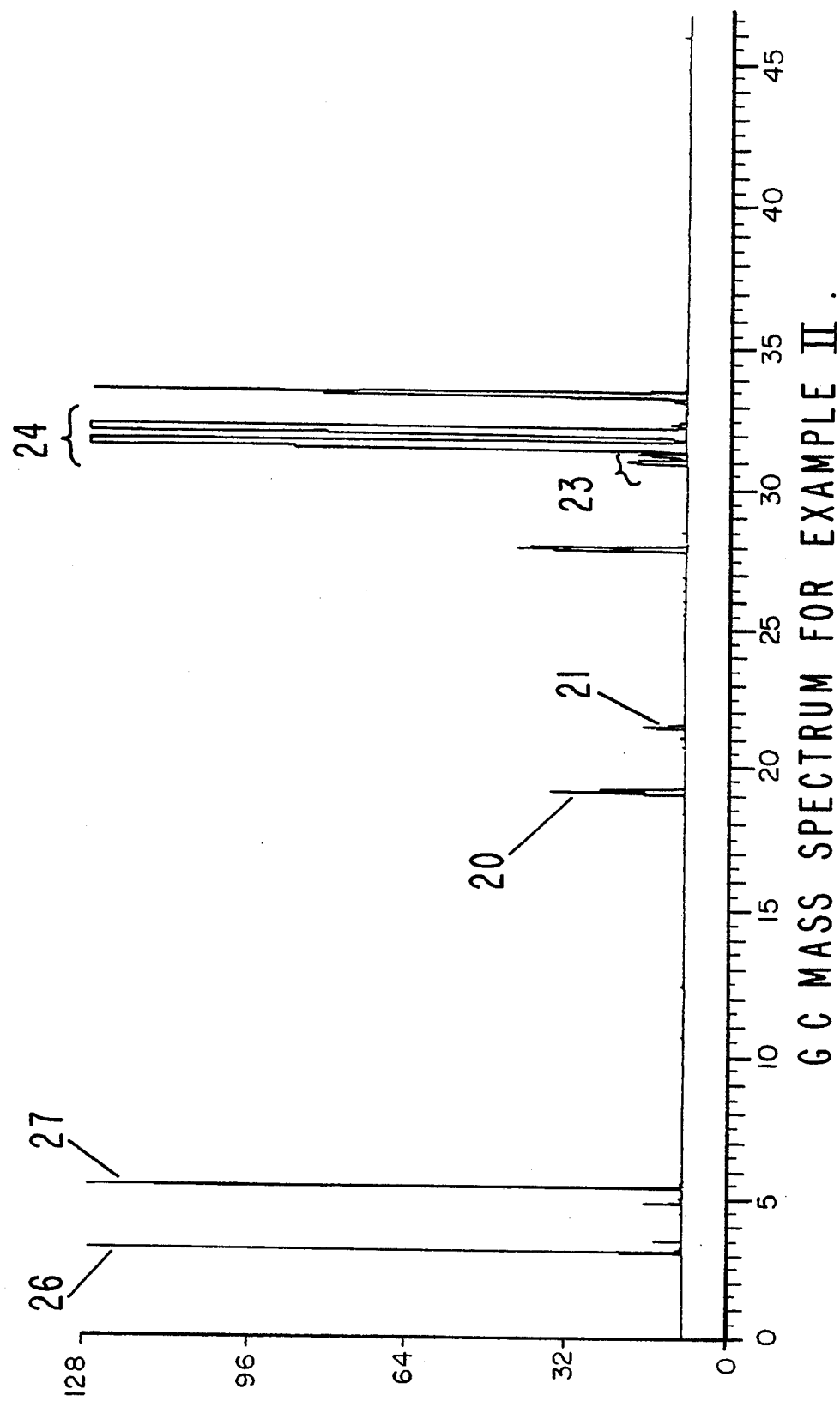

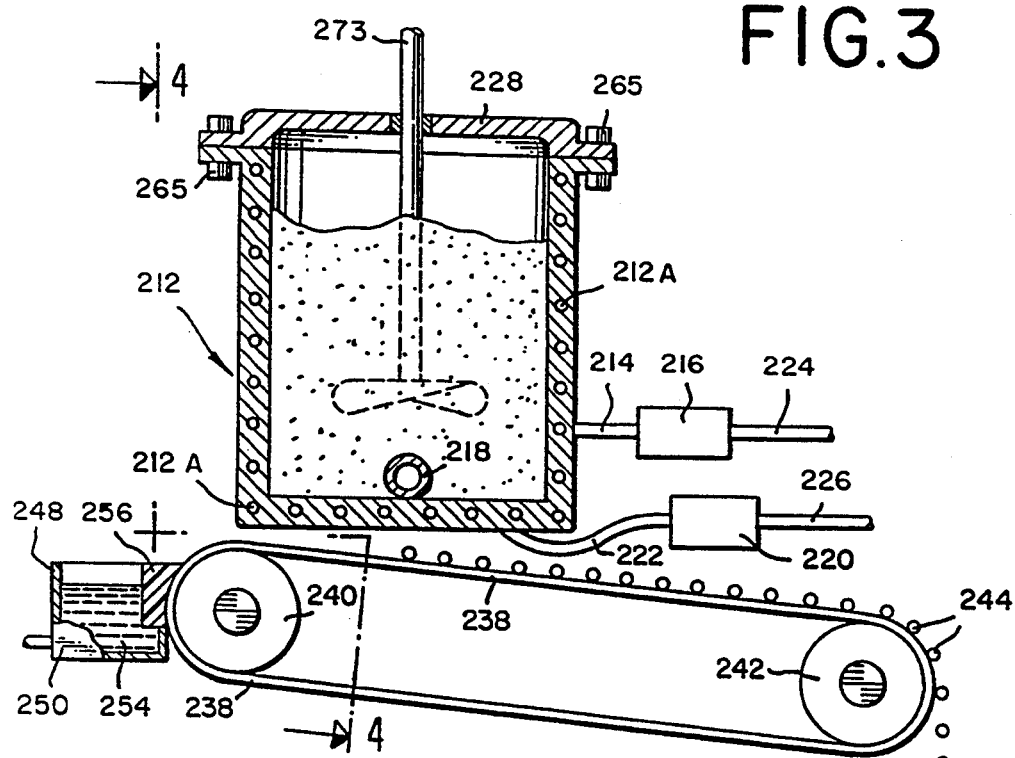
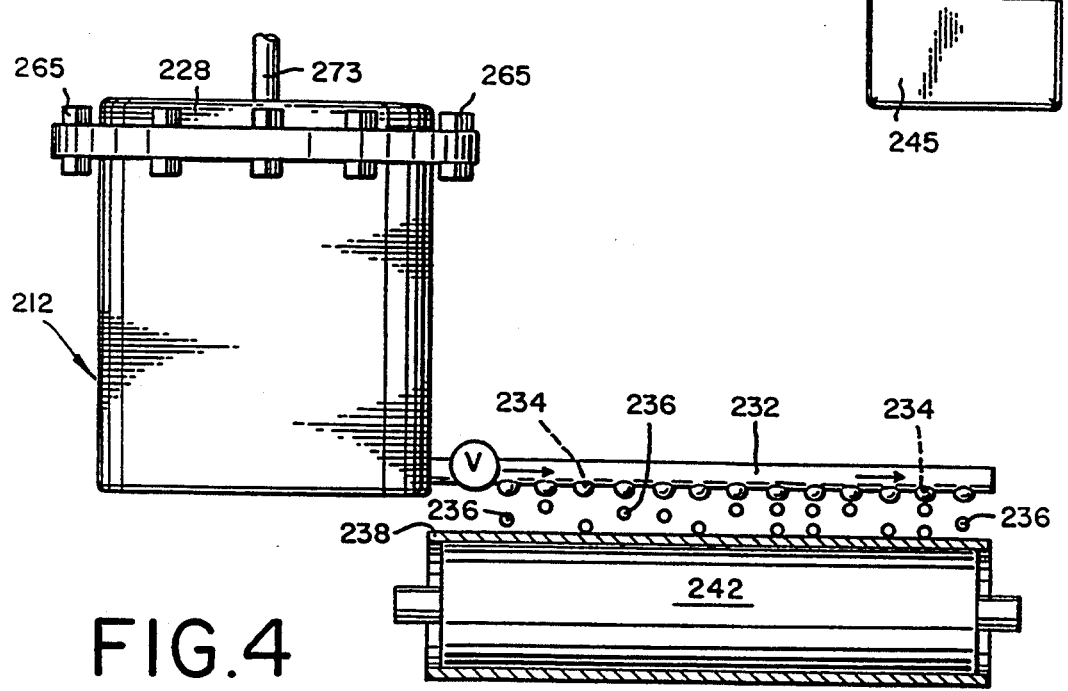

GLC PROFILE FOR EXAMPLE "A".

G C MASS SPECTRUM FOR EXAMPLE "B".

REDUCED REACTION PRODUCT OF PROTONIC ACID CATALYZED REACTION OF METHYL ETHYL KETONE AND BENZALDEHYDE AND PERFUME USES THEREOF

BACKGROUND OF THE INVENTION

Our invention relates to a two-step process for producing phenyl-and cyclohexyl-substituted oxybutane derivative-containing mixtures of our invention by means of first reacting methyl ethyl ketone with benzaldehyde in the presence of a sulfonic acid catalyst to produce a mixture of phenyl pentenone derivatives having the structures:

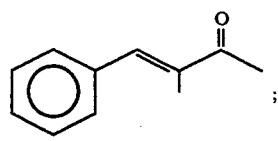
;

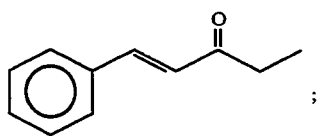
;

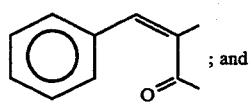
; and

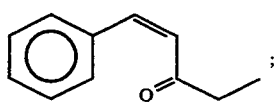
;

and then hydrogenating the resulting mixture of phenyl pentenone derivatives in the presence of a hydrogenation catalyst as well as the product produced thereby which is a mixture of compounds having the structures:

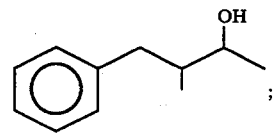
;

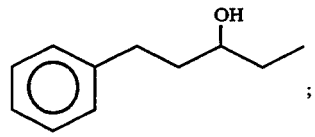
;

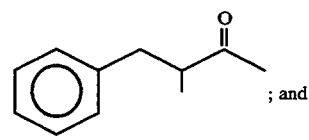
; and

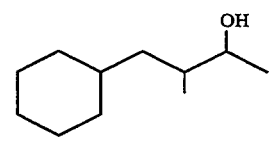

and perfumery uses thereof for augmenting, enhancing or imparting aromas in and to perfume compositions, colognes and perfumed articles.

There has been considerable work performed relating no substances which can be used to impart (modify, augment or enhance) fragrances to (or in) various consumable materials. These substances are used to diminish the use of natural materials, some of which may be in short supply and to provide more uniform properties in the finished product.

Long-lasting substantive intense "wet foral" muguet, rose, green, lilac and ozoney aromas with natural green, floral, muguet and rose topnotes are highly desirable in several types of perfume compositions, perfumed articles and colognes (e.g., muguet fragrances).

Perfume uses of individual phenyl-and cyclohexyl-substituted oxybutane derivative-containing mixtures of our invention are known in the prior art. Thus, Sundt, Swiss Patent 604716 (abstracted at Chem. Abstracts Volume 89:22076g) discloses the perfumery uses of the compound having The structure:

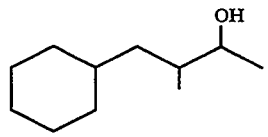

produced from the compound having the structure:

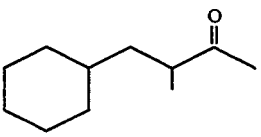

Meuly, et al, U.S. Pat. No. 3,666,255 of Jun. 6, 1972 discloses the perfume use, inter alia, of the compound having the structure:

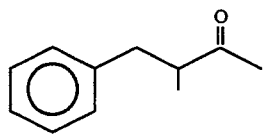

prepared according to the reaction:

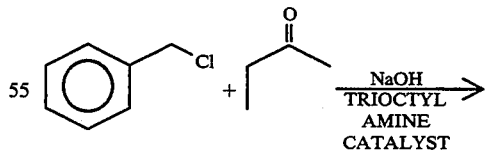

Chmielarz, et al, Chem. Abstracts Volume 83:147254h, abstract of Tluszcze, Srodki, Piorace, Kosmet., 1975, 19(3), pages 109–18 discloses the perfume use of the compound having the structure:

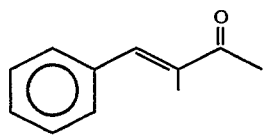

in substantially pure form (98.5–99.5 pure crystalline) prepared according to the reaction:

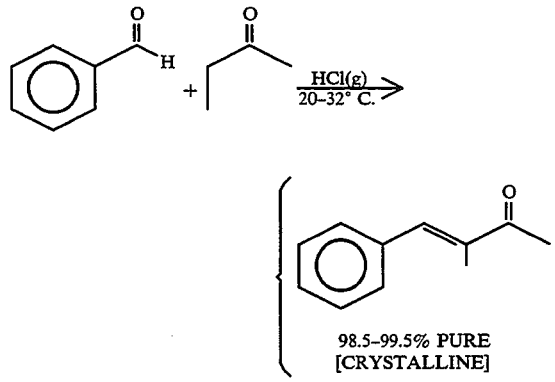

Nothing in the prior art however discloses or infers the unexpected, unobvious and advantageous properties of the phenyl-and cyclohexyl-substituted oxybutane derivative-containing mixtures of our invention prepared according to the process of our invention.

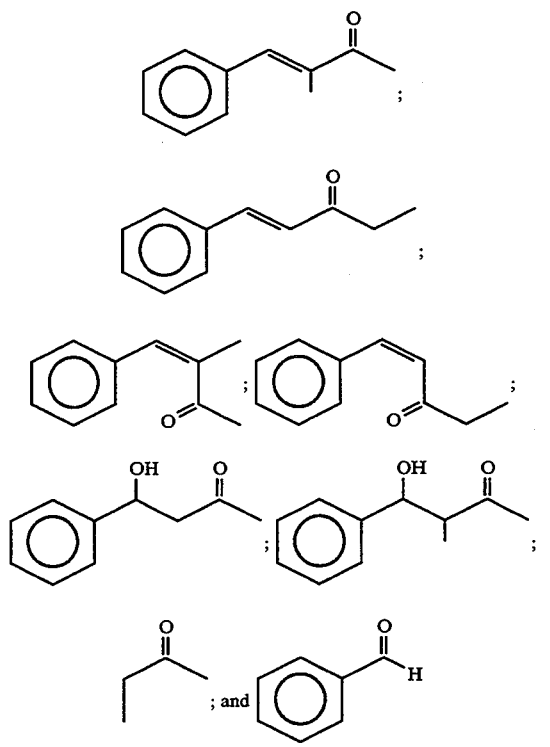

(Conditions: 50 meter×0.32 mm bonded methyl silicone column programmed from 75°–225° C. at 2° C. per minute).

FIG. 2 is the capillary GLC profile for the reaction product (crude) of Example II containing the compounds having the structures:

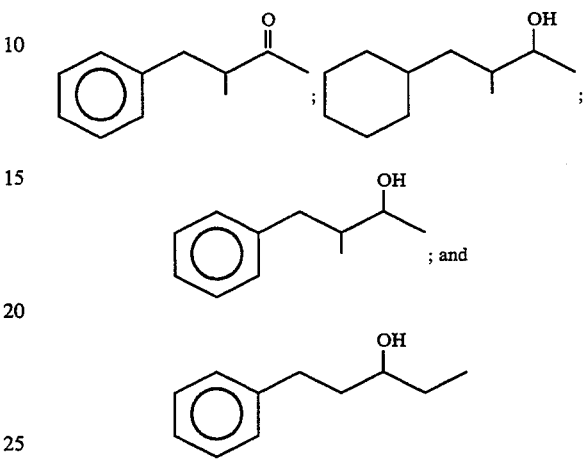

together with the compounds having the structures:

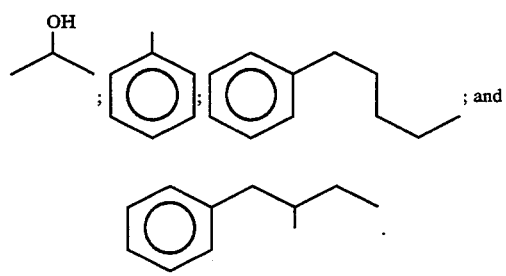

FIG. 3 represents a cut-away side elevation view of apparatus used in forming perfumed polymers which contain imbedded in the interstices of microporous polymers the phenyl-and cyclohexyl-substituted oxybutane derivative-containing mixtures of our invention.

FIG. 4 is a front view of the apparatus of FIG. 3 looking in the direction of the arrows.

Figure 5:
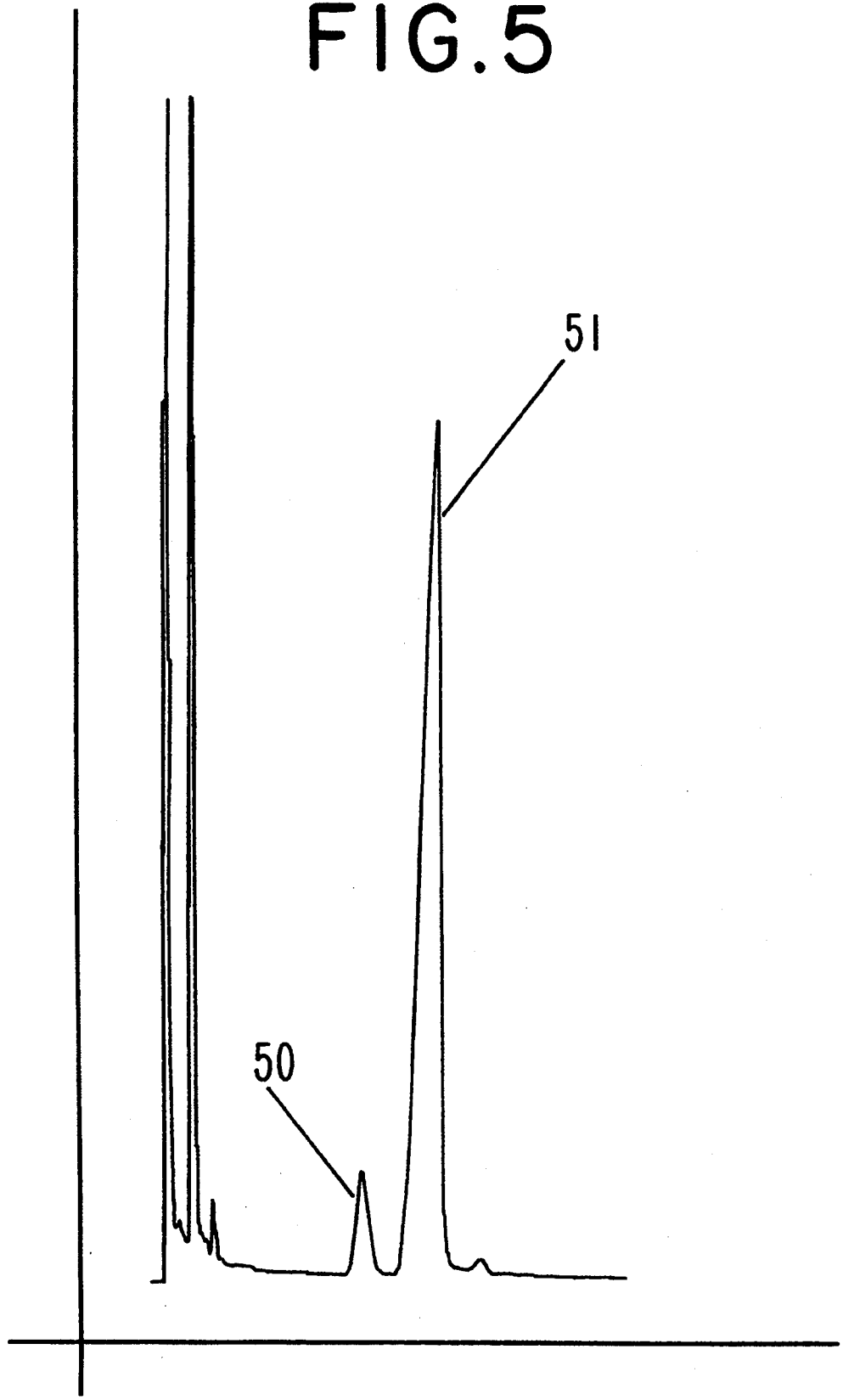

FIG. 5 is the GLC profile of the reaction product of Example A containing the compounds having the structures:

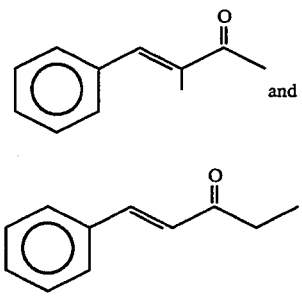

Figure 6:
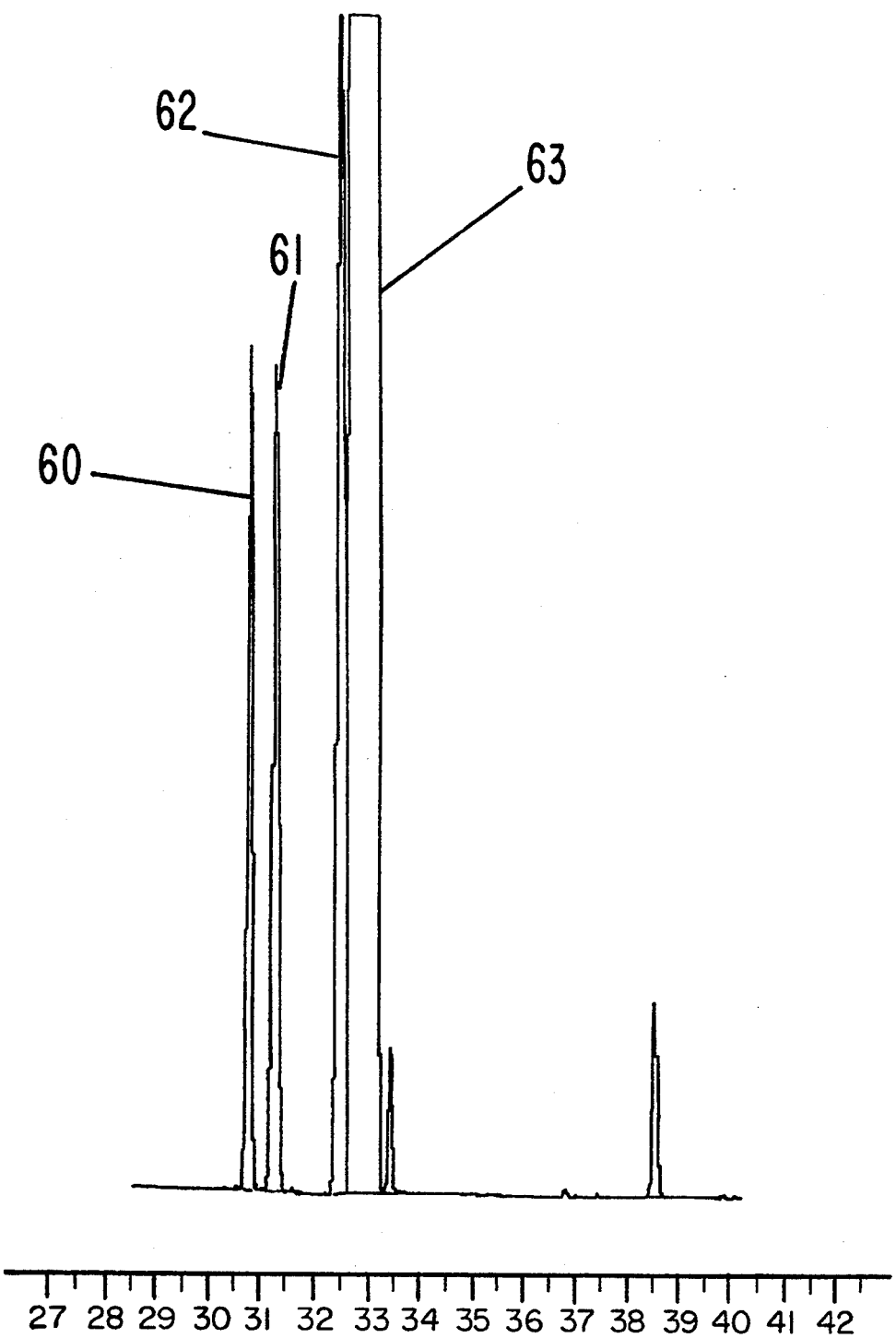

FIG. 6 is the GLC profile for the reaction product of Example B containing the compounds having the structures:

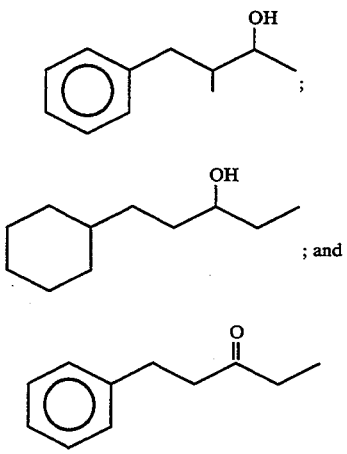

DETAILED DESCRIPTION OF THE DRAWINGS

Figure 1:
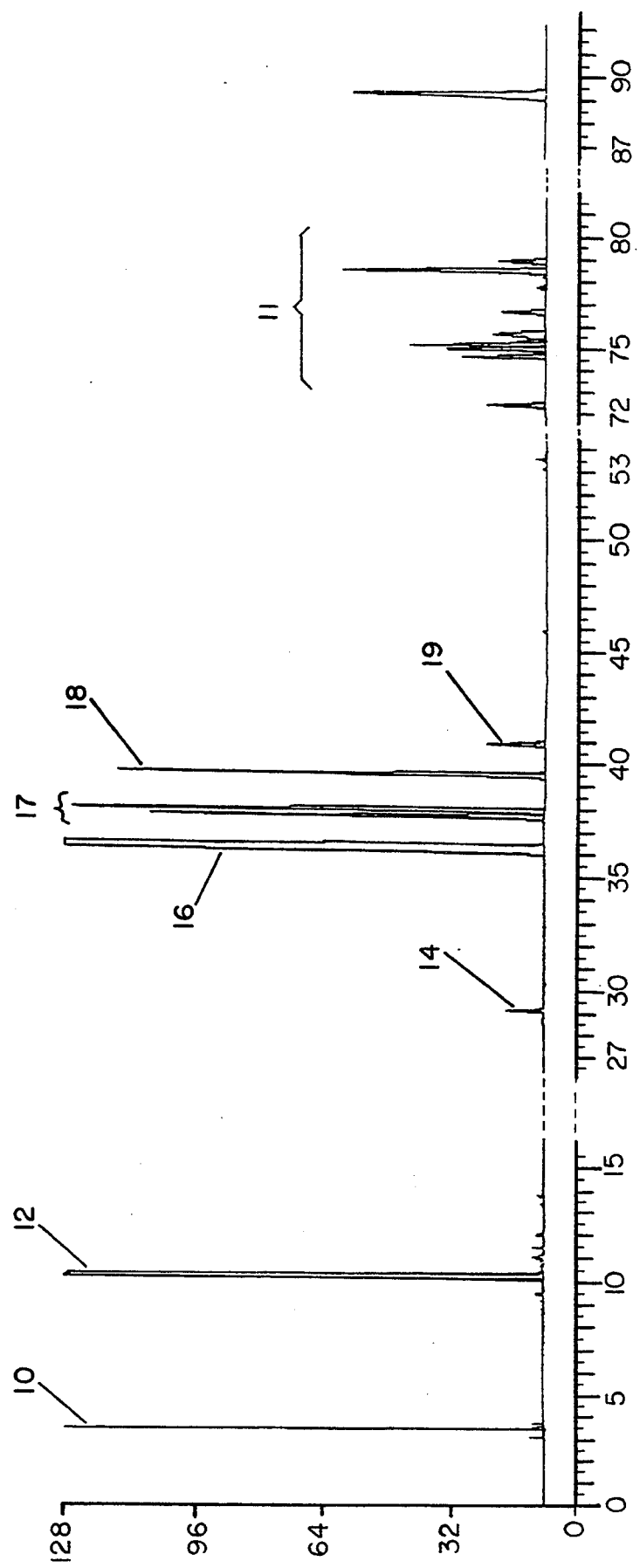
FIG. 1 is the capillary GLC profile for the crude reaction product of Example I containing the compounds having the structures.

Referring to FIG. 1, the capillary GLC profile for crude reaction product of Example I wherein the reaction:

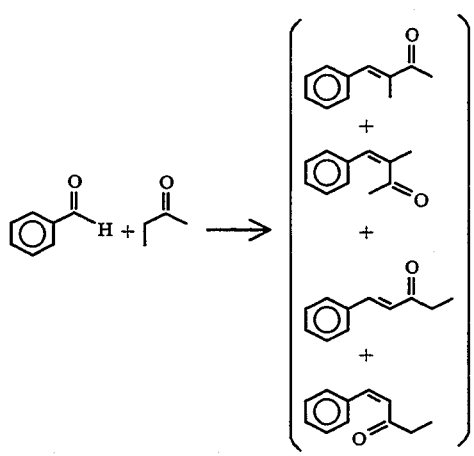

is carried out, the peak indicated by reference numeral 10 is the peak for the methyl ethyl ketone reactant having the structure:

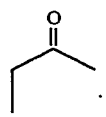

The peak indicated by reference numeral 12 is the peak for the benzaldehyde reactant having the structure:

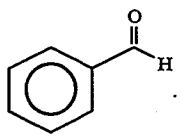

The peak indicated by reference numberal 14 is the peak for the isomer having the structure:

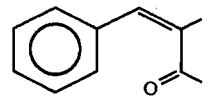

(a "cis" isomer). The peak indicated by reference numberal 16 is the peak for the isomer having the structure:

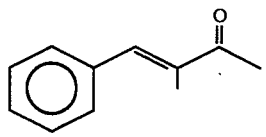

(the "trans" isomer). The peaks indicated by reference numeral 17 are peaks for stereo isomers of the compound having the structure:

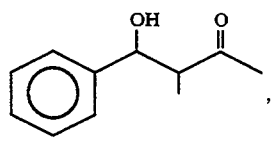

for example, the stereo isomer having the structure:

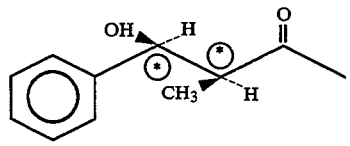

The peak indicated by reference numberal 18 is the peak for the compound having the structure:

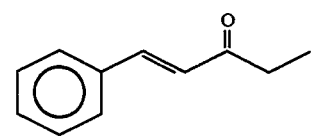

The peak indicated by reference numberal 19 is the peak for if the compound having the structure:

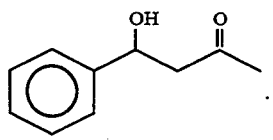

Peaks indicated by means of reference numberal 11 are peaks for "high boilers".

Referring to FIG. 2, the capillary GLC profile for the crude reaction product of Example II wherein the reaction:

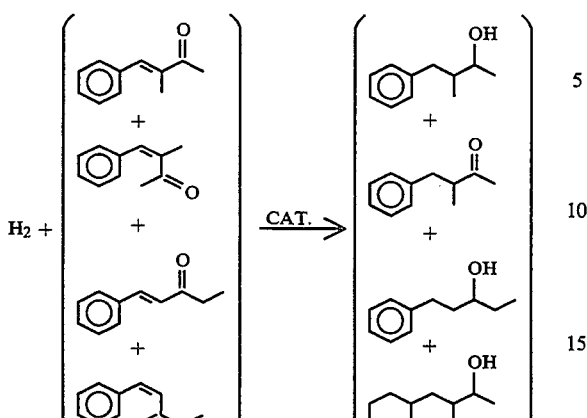

is exemplified, the peak indicated by reference numberal 26 is the peak for the isopropyl alcohol solvent having the structure:

The peak indicated by reference numberal 27 is the peak for toluene. The peak indicated by reference numberal 20 is the peak for the hydrocarbon side product having the structure:

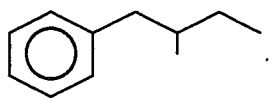

The peak indicated by reference numberal 21 is the peak for the hydrocarbon side product having the structure:

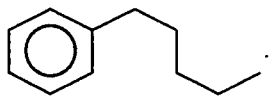

The peak indicated by reference numberal 22 is the peak for the compound having the structure:

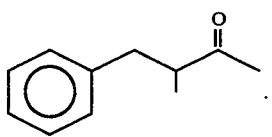

The peaks indicated by reference numberal 23 are for stereo isomers of the compound having the structure:

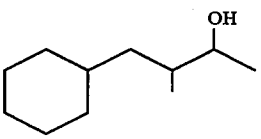

The peaks indicated by reference numberal 24 are for the stereo isomers of the compound having the structure:

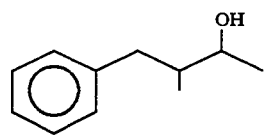

The peak indicated by reference numberal 25 is the peak for the compound having the structure:

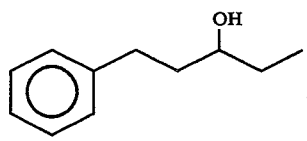

Referring to FIG. 5, the GLC profile for the reaction product of Example A, the peak indicated by reference numeral 50 is for the compound having the structure:

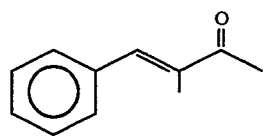

The peak indicated by reference numberal 51 is for the compound having the structure:

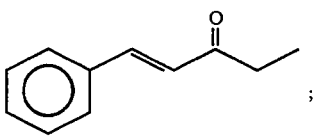

Example A being an exemplification of the reaction:

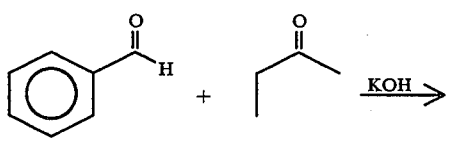

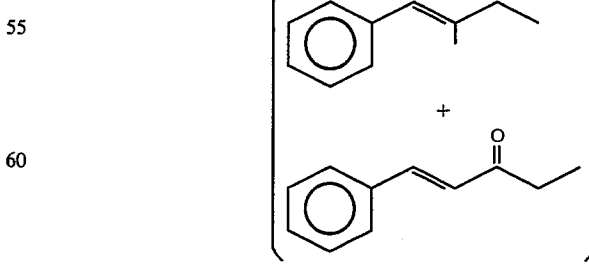

Referring to FIG. 6, FIG. 6 is the GLC profile of the reaction product of Example B, exemplifying the reaction:

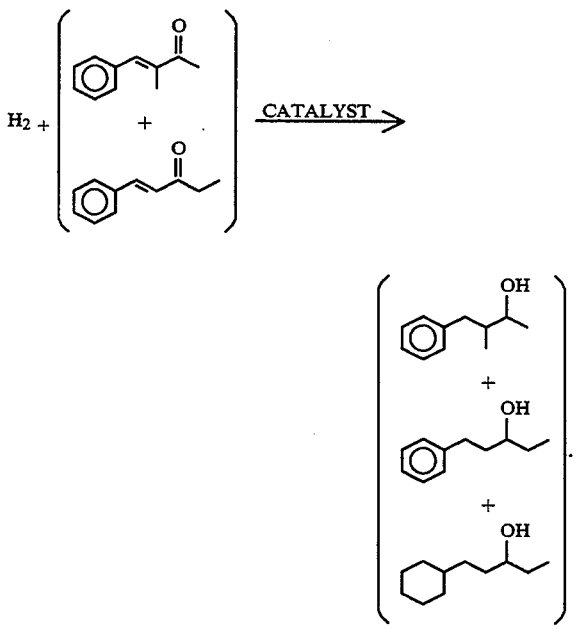

The peaks indicated by reference numerals 60 and 61 are for stereo isomers of the compound having the structure:

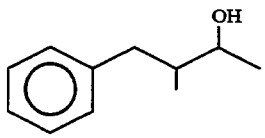

The peak indicated by reference numbaral 62 is for the compound having the structure:

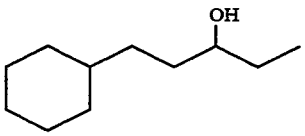

The peak indicated by reference numbaral 63 is for the compound having the structure:

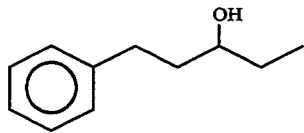

Referring to FIGS. 3 and 4 there is provided a process for forming scented polymer elements (wherein the polymer may be a thermoplastic polymer such as low density polyethylene or polypropylene or copolymers of ethylene and vinyl acetate or mixtures of polymers and copolymers such as copolymers of ethylene and vinyl acetate and polyethylene) such as pellets useful in the formation of plastic particles useful in fabricating certain articles which may be perfumed. This process comprises heating the polymer or mixture of polymers to the melting point of said polymer or mixture of polymers, e.g., 250° C. in the case of low density polyethylene. The lower most portion of the container is maintained at a slightly lower temperature and the material in the container is taken off at such location for delivery through the conduit. Thus, referring to FIGS. 3 and 4, in particular, the apparatus used in producing such elements comprises a device for forming the polymer containing the perfume, e.g., polyethylene or poly-ethylene-polyvinyl acetate or mixtures of same or polypropylene, which comprises a vat or container 212 into which the polymer taken alone or in admixture with other copolymers and the perfuming substance which is the phenyl-and cyclohexyl-substituted oxybutane derivative-containing mixture of our invention and other compatible perfumes is placed. The container is closed by means of an air-tight lid 228 and clamped to the container by bolts 265. A stirrer 273 traverses the lid or cover 228 in an air-tight manner and is rotatable in a suitable manner. A surrounding cylinder having heating heating coils 212A which are supplied with electric current through cable 214 from a rheostat or control 216 is operated to maintain the temperature inside the container 212 such that the polymer in the container will be maintained in the molten or liquid state. It has been found advantageous to employ polymers at such a temperature that the viscosity will be in the range of 90–100 sayboldt seconds. The heater is operated to maintain the upper portion of the container 212 within a temperature range of, for example, 220°–270° C. in the case of low density polyethylene. The bottom portion of the container 212 is heated by means of heating coils 212A regulated through the control 220 connected thereto through a connecting wire 222 to maintain the lower portion of the container 212 within a temperature range of 220°–270° C.

Thus, the polymer or mixture of polymers added no the container 212 is heated from 10–12 hours, whereafter the perfume composition of perfume material which contains an least the phenyl-and cyclohexyl-substituted oxybutane derivative-containing mixtures of our invention is quickly added to the melt. Generally, about 10–45 percent by weight of the resulting mixture of the perfumery substance is added to the polymer.

After the perfume material is added to the container 212, the mixture is stirred for a few minutes, for example, 5–15 minutes and maintained within the temperature ranges indicated previously by the heating coil 212A. The controls 216 and 220 are connected through cables 224 and 226 to a suitable supply of electric current for supplying the power for heating purposes. Thereafter, the valve "V" is opened permitting the mass to flow outwardly through conduit 232 having a multiplicity of orifices 234 adjacent to the lower side thereof. The outer end of the conduit 232 is closed so that the liquid polymer in intimate admixture with the phenyl- and cyclohexyl-substituted oxybutane derivative-containing mixtures of our invention and one or more other substances, will continuously drop through the orifices 234 downwardly from the conduit 232 (also indicated by reference numbaral 218 in FIG. 3). During This time, the temperature of the polymer intimately admixed with the perfumery substance in the container 212 is accurately controlled so that a temperature in the range of from about 240°–250° C., for example, (in the case of low density polyethylene) will exist in the conduit 232. The regulation of the temperature through the controls 216 and 220 is essential in order to insure the temperature balance to provide for the continuous dripping or dropping of molten polymer intimately admixed with the perfume substance which is all or which contains the phenyl-and cyclohexyl-substituted oxybutane derivative-containing mixtures of our invention, through the orifices 234 at a rate which will insure the formation of droplets 236 which will fall downwardly onto a moving conveyor belt 238 caused to run between conveyor wheels 240 and 242 beneath the conduit 232.

When the droplets 236 fall onto the conveyor 238, they form pellets 244 which harden almost instantaneously and fall off the end of the conveyor 238 into container 245 which is advantageously filled with water or some other suitable cooling liquid to insure the rapid cooling of each of the pellets 244. The pellets 244 are then collected from the container 245 and utilized for the formation of functional products, e.g., garbage bags and the like. Container 250 is optionally utilized whereby cooling liquid 254 contained in container 250 maintained within the side wall 248 is absorbed into sponge 256 which cools belt 238.

THE INVENTION

Our invention is drawn to a two-step process for producing phenyl-and cyclohexyl-substituted oxybutane derivative-containing mixture, useful in perfumery, by means of first reacting methyl ethyl ketone with benzaldehyde in the presence of a sulfonic acid catalyst to produce a mixture of phenyl pentenone derivatives having the structures:

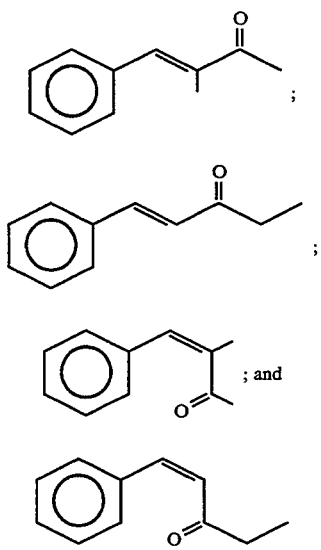

and then hydrogenating the resulting mixture of phenyl pentenone derivatives in the presence of a hydrogenation catalyst to produce a mixture of compounds having the structures:

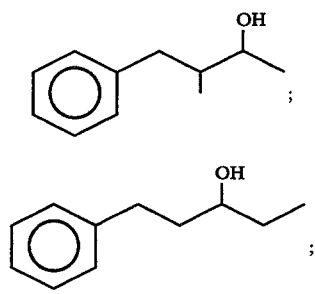

-continued

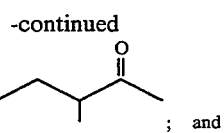 ; and

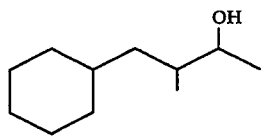.

More specifically, our invention is drawn to a process for forming phenyl-and cyclohexyl-substituted oxybutane derivative-containing mixtures comprising the steps of:

1. first reacting methyl ethyl ketone with benzaldehyde in the presence of a sulfonic acid catalyst at a temperature of from about 20° C. up no about 90° C. for a period of time of from about one hour up to about six hours with the mole ratio of methyl ethyl ketone:benzaldehyde reactants being from about 1:1 up to about 3:1 and with the number of moles of sulfonic acid per mole of benzaldehyde being from about 0.1 up to about 0.4 according to the reaction:

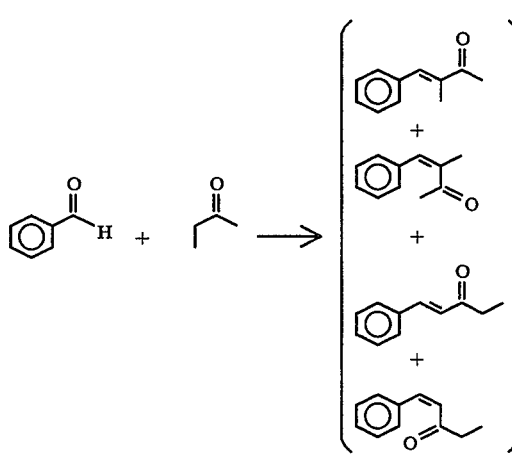

thereby forming a first mixture of phenyl pentenone derivatives having the structures:

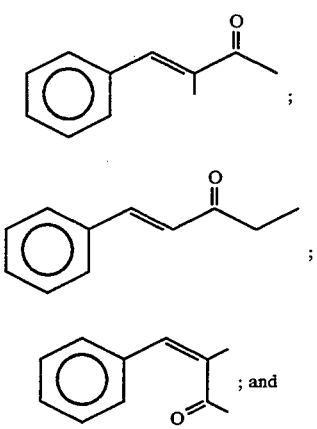

-continued

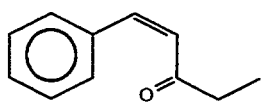

with the ratio of the compounds having the structures:

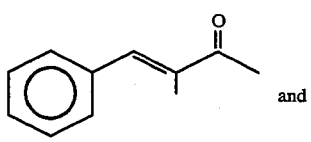
and
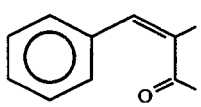
:

the compounds having the structures:

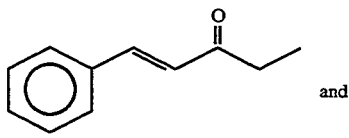
and
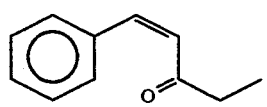

being from about 88:12 to about 95:5 and the ratios of the compounds having the structure:

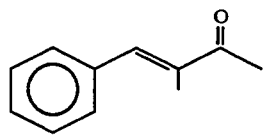
:

the compound having the structure:

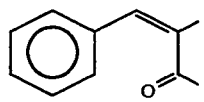

and the ratio of the compound having the structure:

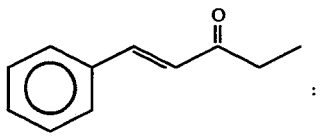
:

the compound having the structure:

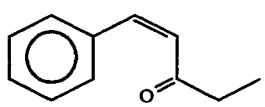

being 98:2; and then 2. reacting the first mixture of phenyl pentenone derivatives with hydrogen at a temperature of from about 150° C. up to about 200° C., at a pressure of from about 250 psig (pounds per square inch gauge) up to about 600 psig for a time of from about one hour up to about ten hours in the presence of a hydrogenation catalyst selected from the group consisting of:

(a) Raney nickel; and
(b) copper chromite according to the reaction:

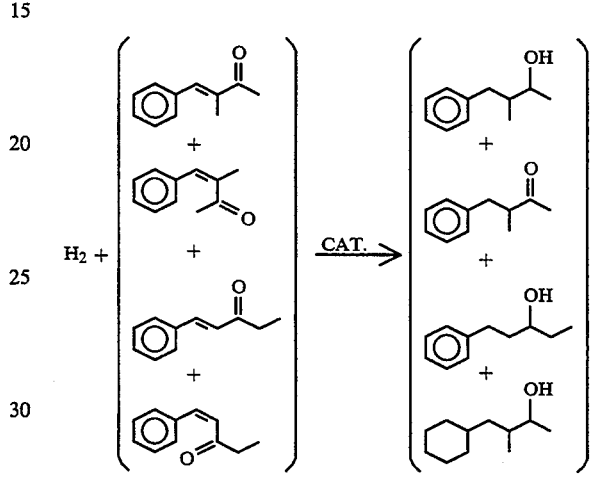

whereby phenyl- and cyclohexyl-substituted oxybutane derivative-containing mixture is formed containing:

about 80–95 weight percent of the compound having the structure:

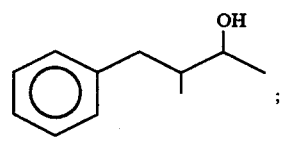
;

about 4–12 weight percent of the compound having the structure:

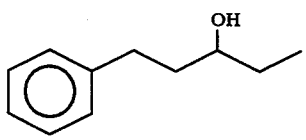
;

about 1–5 weight percent of the compound having the structure:

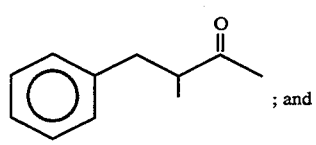
; and about 1–5 weight percent of the compound having the structure:

With respect to the first step, than is, the reaction of methyl ethyl ketone with benzaldehyde, the sulfonic acid useful in the practice of our invention may be:

60–90% sulfuric acid;
para-toluene sulfonic acid;
methane sulfonic acid; or
xylene sulfonic acid.

As stated, supra, the period of time of reaction may vary from about 1 up to about 6 hours. However, a preferable period of time of reaction is from about 2 up to about 4 hours.

The reaction product resulting from the reaction of the methyl ethyl ketone and benzaldehyde yields the isomers having the structures:

The mole ratios of the compounds having the structures:

to the compounds having the structures:

vary from about 80:12 up to about 95:5. The mole ratios of the "trans" to "cis" reaction products are about 98:2. More specifically, the mole ratio of the compound having the structure:

to the compound having the structure:

is about 98:2. By the same token, the mole ratio of the compound having the structure:

the compound having the structure:

is also about 98:2.

The hydrogenation reaction, to wit:

as stated, supra, may vary insofar as the time of reaction from about 1 hour up to about 10 hours with a preferable time of reaction being between 6 and 9 hours. The reaction may take place in the presence of any alcohol solvent such as an isopropyl alcohol solvent; or the reaction may take place in the absence of solvent.

The phenyl-and cyclohexyl-substituted oxybutane derivative-containing mixture of our invention has uses in augmenting, enhancing or imparting an aroma of or to perfume compositions, colognes and perfumed articles including but not limited to perfumed polymers, cosmetic powders, anionic, cationic, non-ionic or zwitterionic detergents, fabric softener compositions, fabric softener articles including drier-added fabric softener articles (e.g., BOUNCE ® marketed by the Procter & Gamble Company of Cincinnati, Ohio).

The phenyl-and cyclohexyl-substituted oxybutane derivative-containing mixture of our invention is capable of imparting, augmenting or enhancing intense and long-lasting "wet floral", muguet, rose, green, lilac and ozoney aromas with natural green, floral, muguet and rose topnotes to perfume compositions, colognes and perfumed articles including soaps, anionic, cationic, nonionic or zwitterionic detergents, fabric softener articles and other perfumed articles.

The phenyl-and cyclohexyl-substituted oxybutane derivative-containing mixture of our invention gives rise to unexpected, unobvious and advantageous perfumery properties when compared with single compounds known in the prior arm to be useful in augmenting, enhancing or imparting aromas to perfume compositions, colognes and perfumed articles. Furthermore, when other processes are used to prepare such mixtures of phenyl-and cyclohexyl-substituted oxybutane derivative-containing mixture, completely different results ensue. Thus, for example, when carrying out a first reaction to form phenyl pentenone derivatives, thusly:

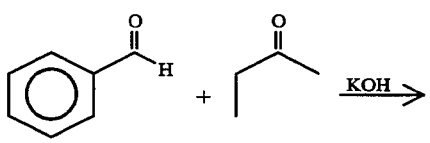

followed by a hydrogenation reaction, thusly:

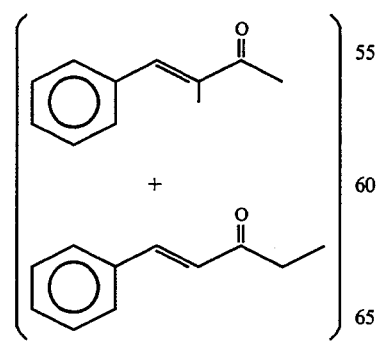

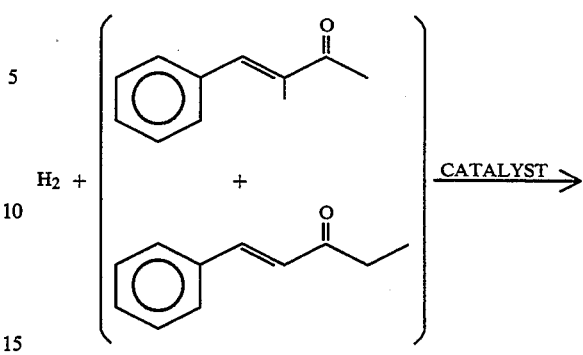

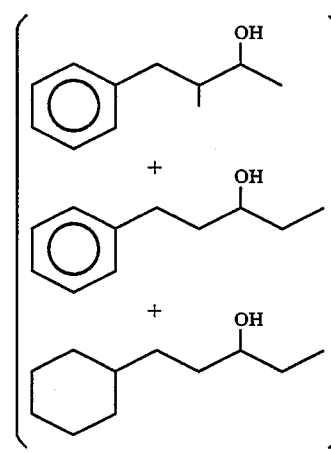

whereby the compounds having the structures:

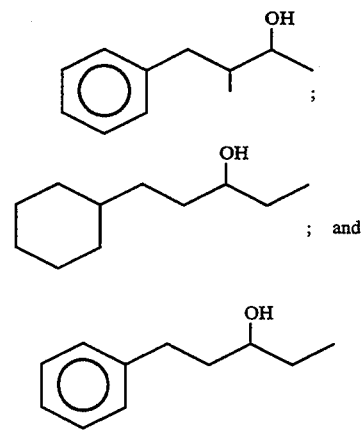

are produced, such compounds are produced in proportions completely different from those produced using the instant invention. Furthermore, using the process of our invention no compound having the structure:

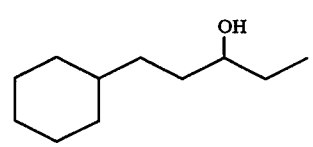

is produced The only cyclohexyl pentanol produced has the structure:

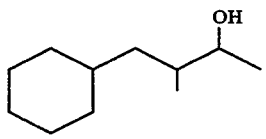

The resulting mixture of compounds having the structures:

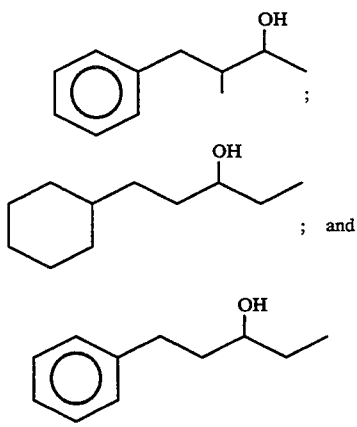

has a sweet, cinnamon, blackberry and raspberry aroma with sweet, fruity and rose topnotes. On a scale of 1–10, the quality of such mixture has a value of "5"; the substantivity of such mixture has a value of "4" and the intensity has a value of "5". On the other hand, the phenyl-and cyclohexyl-substituted oxybutane derivative-containing mixture of our invention, on a scale of 1–10 has a quality of "9"; an intensity of "9" and a substantivity of "10".

The phenyl-and cyclohexyl-substituted oxybutane derivative-containing mixture of our invention and one or more auxiliary perfume ingredients, including, for example, hydrocarbons, other alcohols, other ketones, aldehydes, nitriles, esters, lactones, ethers, hydrocarbons, synthetic essential oils and natural essential oils may be admixed so that the combined odors of the individual components produce a pleasant and desired fragrance particularly and preferably in the "green, woody, floral fragrance" area. Such perfume compositions usually contain (a) the main note or the "bouquet" or foundation stone of the composition; (b) modifiers which round off and accompany the main note; (c) fixatives which include odorous substances which lend a particular none to the perfume throughout all stages of evaporation and substances which retard evaporation; and (d) topnotes which are usually low boiling, fresh smelling materials.

In perfume compositions, it is the individual components which contribute to their particular olfactory characteristics, however, the overall sensory effect of the perfume composition will be at least the sum total of the effects of each of the ingredients. Thus, the phenyl-and cyclohexyl-substituted oxybutane derivative-containing mixtures of our invention can be used to alter, modify or enhance the aroma characteristics of a perfume composition, for example, by utilizing or moderating the olfactory reaction contributed by another ingredient in the composition.

The amount of the phenyl-and cyclohexyl-substituted oxybutane derivative-containing mixture of our invention which will be effective in perfume compositions as well as in perfumed articles and colognes depends on many factors, including the other ingredients, their amounts and the effects which are desired. It has been found that perfume compositions containing as little as 0.05% of the phenyl-and cyclohexyl-substituted oxybutane derivative-containing mixture of our invention can be used impart intense and long-lasting "wet floral", muguet, rose green, lilac and ozoney aromas with natural green, floral, muguet and rose topnotes to soaps, cosmetics, detergents (including anionic, cationic, nonionic or zwitterionic solid or liquid detergents) or other products. The amount employed can range up no 70% of the fragrance components and will depend upon considerations of cost, nature of the end product, the effects desired on the finished product and the particular fragrance sought.

The phenyl-and cyclohexyl-substituted oxybutane derivative-containing mixture of our invention is useful (taken alone or together with other ingredients in perfume compositions) in detergents and soaps, space odorants and deodorants, perfumes, colognes, toilet water, bath preparations such as lacquers, brillantines, pomades and shampoos, cosmetic preparations such as creams, deodorants, hand lotions and sun screens; powders, such as talcs, dusting powders, face powders and the like.

As little as 0.7% of the phenyl-and cyclohexyl-substituted oxybutane derivative-containing mixture of our invention will suffice to impart an intense and substantive "wet floral", muguet, rose, green, lilac and ozoney aroma with natural green, floral, muguet and rose topnotes to floral, green perfume formulations. Generally, no more than 5% of the phenyl-and cyclohexyl-substituted oxybutane derivative-containing mixture of our invention based on the ultimate end produce is required to be used "as is" or in the perfume composition.

Furthermore, as little as 0.25% of the phenyl-and cyclohexyl-substituted oxybutane derivative-containing mixture of our invention will suffice to impart such aroma to perfumed articles per se, whether in the presence of other perfume materials or whether used by themselves. Thus, the range of use of the phenyl-and cyclohexyl-substituted oxybutane derivative-containing mixture of our invention in perfumed articles may vary from about 0.25% up to about 5% based on the total weight of the perfumed article.

In addition, the perfume composition or fragrance compositions of our invention can contain a vehicle or carrier for the phenyl-and cyclohexyl-substituted oxybutane derivative-containing mixture of our invention. The vehicle can be a liquid such as a non-toxic alcohol, e.g., ethanol, a non-toxic glycol, e.g., propylene glycol or the like. The carrier can also be an absorbent solid, such as a gum (e.g., gum arabic, guar gum or xanthan gum), or components for encapsulating the composition, as by means of coacervation (using, for example, a gelatin coacervation agent).

It will thus be apparent that the phenyl-and cyclohexyl-substituted oxybutane derivative-containing mixture of our invention can be utilized to alter, modify or enhance the aroma of perfume compositions, colognes or perfumed articles.

The following Examples A and B serve to illustrate processes for production of phenyl-and cyclohexyl-substituted oxybutane derivative-containing mixture other than the phenyl-and cyclohexyl-substituted oxybutane derivative-containing mixture of our invention. Examples I and II serve to illustrate a specific embodiment for preparing the phenyl-and cyclohexyl-substituted oxybutane derivative-containing mixture of our invention. Examples following Example II illustrate specific embodiments for utilization of the phenyl-and cyclohexyl-substituted oxybutane derivative-containing mixture of our invention in perfumery. It will be understood that these examples are illustrative and that the invention is to be considered to be restricted thereto only as indicated in the appended claims.

All parts and percentages given herein are by weight unless otherwise specified.

EXAMPLE A
PREPARATION OF PHENYL PENTENONE DERIVATIVES

Reaction

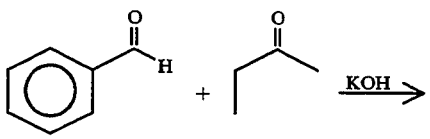

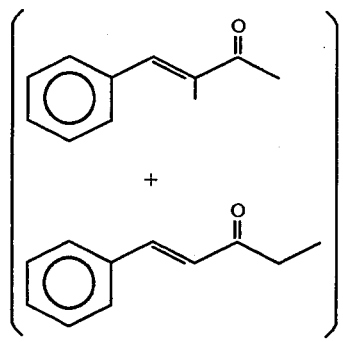

Into a 2 liter reaction vessel equipped with stirrer, thermometer, reflux condenser and heating mantle are placed 12 grams (0.21 moles) of potassium hydroxide and 300 grams of methyl alcohol.

While maintaining the reaction mass at 25° C., 6.0 moles (636 grams) of benzaldehyde is added with stirring.

Over a period of two hours, 432 grams of methyl ethyl ketone is added to the reaction mass while maintaining the reaction mass at 25°-30° C. The reaction mass is then maintained at 30° C. with stirring for a period of one hour.

The reaction mass is then washed with 500 ml water yielding two phases; an organic phase and an aqueous phase. The organic phase is separated from the aqueous phase and dried over anhydrous magnesium sulfate.

The resulting product is then distilled on a fractional distillation column yielding the following fractions:

| Fraction No. | Vapor Temp. (°C.) | Liquid Temp. (°C.) | Vacuum mm/Hg. Pressure |
|---|---|---|---|
| 1 | 23/40 | 23/120 | 15.0/1.0 |
| 2 | 85 | 140 | 4 |
| 3 | 123 | 144 | 2 |
| 4 | 123 | 142 | 2 |
| 5 | 121 | 153 | 1 |
| 6 | 107 | 178 | 0.21 |
| 7 | 119 | 218 | 0.23 |
| 8 | 145 | 230 | 0.25. |

Fractions 3–6 are bulked. NMR, IR and mass spectral analysis yield the information that the resulting product (bulked distillation Fractions 3–6) have the structures:

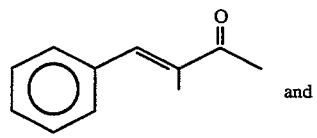 and

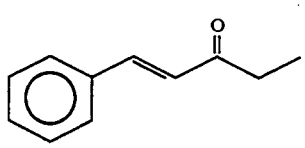

EXAMPLE B
PREPARATION OF PHENYL-AND CYCLOHEXYL-SUBSTITUTED OXYBUTANE DERIVATIVE-CONTAINING MIXTURE

Reaction

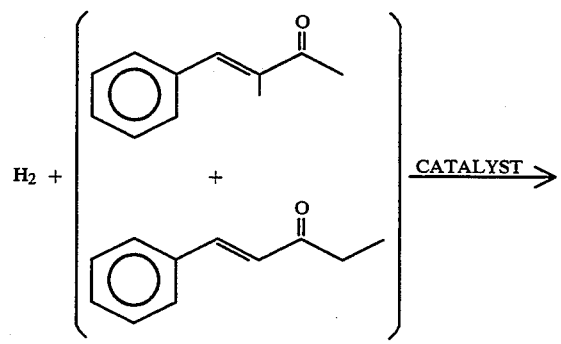

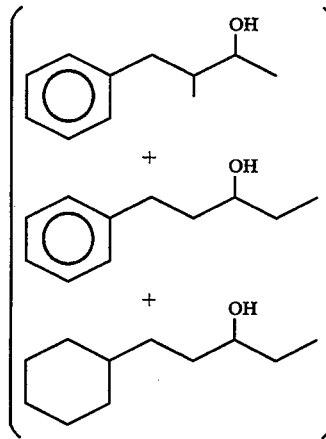

Into an 1 liter autoclave are placed the following materials:

240 grams of the mixture of compounds having the structures:

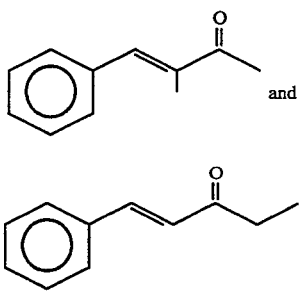

and prepared according to Example A;
225 grams of isopropyl alcohol; and
2.0 grams of Raney Nickel.

The autoclave is closed and hydrogen is pumped into the autoclave while maintaining the reaction temperature an 125°-130° C. and maintaining the pressure at 400 pounds per square inch gauge (psig).

The reaction is carried out for a period of five hours.

At the end of the five hour period, the autoclave is cooled and opened and the reaction mass is filtered.

The resulting filtrate is then fractionally distilled on a fractional distillation column yielding the following fractions:

| Fraction No. | Vapor Temp. (°C.) | Liquid Temp. (°C.) | Vacuum mm/Hg. Pressure |
| --- | --- | --- | --- |
| 1 | 23/27 | 23/120 | 120/20 |
| 2 | 92 | 124 | 2 |
| 3 | 96 | 126 | 3 |
| 4 | 96 | 126 | 3 |
| 5 | 96 | 126 | 3 |
| 6 | 98 | 126 | 3 |
| 7 | 96 | 127 | 3 |
| 8 | 97 | 128 | 3 |
| 9 | 99 | 130 | 3 |
| 10 | 99 | 130 | 3 |
| 11 | 99 | 140 | 3. |

Distillation fractions 3-8 are bulked. Bulked distillation fractions are a mixture of the compounds having the structures:

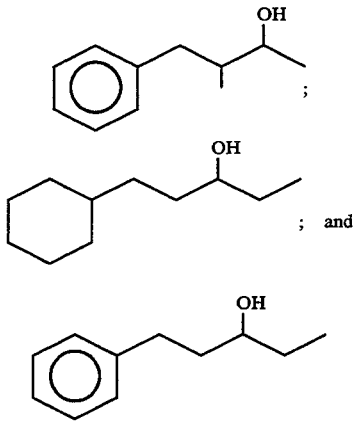

as confirmed by NMR, IR and mass spectral analysis.

The resulting product has a sweet, cinnamon, blackberry and raspberry aroma profile with sweet, fruity and rose topnotes.

EXAMPLE I

PREPARATION OF PHENYL PENTENONES

Reaction

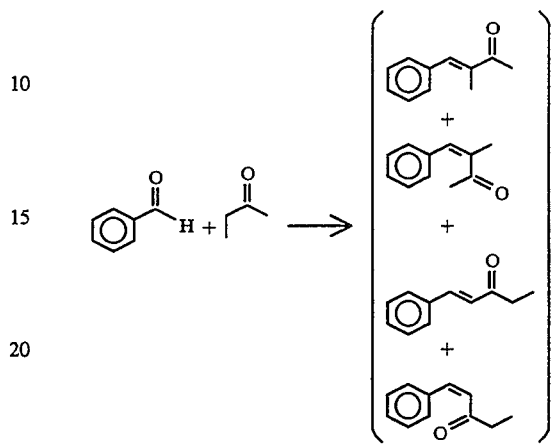

Into a 3 liter reaction vessel equipped with stirrer, thermometer, reflux condenser and heating mantle is placed a mixture of 864 grams methyl ethyl ketone (12.0 moles); 66 grams of 90% sulfuric acid (0.63 moles) and 22 grams of water. The resulting mixture is heated to 60° C. and over a period of three hours while maintaining the reaction mass at 60° C., 1060 grams of benzaldehyde (10.0 moles) is added to the reaction mass.

The reaction mass is then maintained at a temperature of 60° C. for a period of one hour.

Over a period of 0.5 hours while maintaining the reaction mass at 60° C., an additional 60 grams of 90% sulfuric acid is added to the reaction mass.

The reaction mass is then maintained at 60° C. with stirring for a period of 1.5 hours.

At the end of the 1.5 hour period the reaction mass is admixed with 175 grams of water. The reaction mass is then washed with 175 grams of a 10% aqueous sodium bicarbonate solution. The organic phase is separated from the aqueous phase and the organic phase is dried over anhydrous magnesium sulfate and then fractionally distilled on a fractional distillation column yielding the following fractions:

| Fraction No. | Vapor Temp. (°C.) | Liquid Temp. (°C.) | Vacuum mm/Hg. Pressure |
| --- | --- | --- | --- |
| 1 | 23/33 | 23/100 | 2.00/1.00 |
| 2 | 72 | 125 | 1 |
| 3 | 73 | 125 | 1 |
| 4 | 118 | 189 | 0.3. |

The resulting product is a mixture of compounds having the structures:

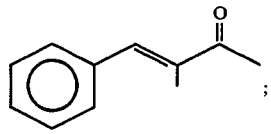

-continued

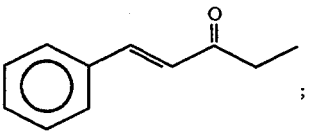;

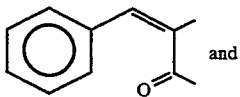 and

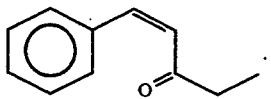

The resulting product is then utilized in Example II.

EXAMPLE II

PREPARATION OF PHENYL-AND CYCLOHEXYL-SUBSTITUTED OXYBUTANE DERIVATIVE-CONTAINING MIXTURE

Reaction

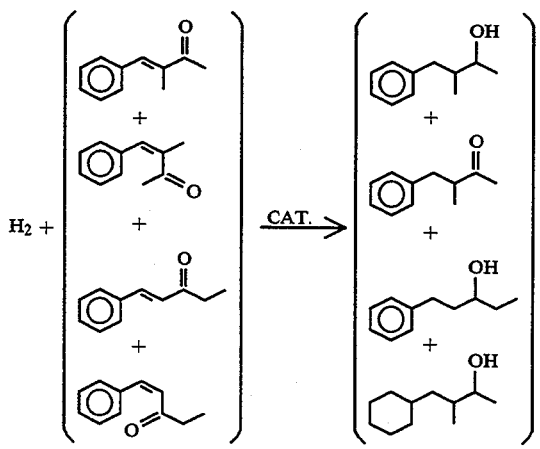

An 1 liter autoclave is charged with 355 grams of the mixture of compounds having the structures:

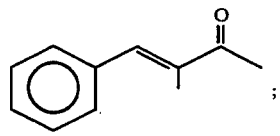;

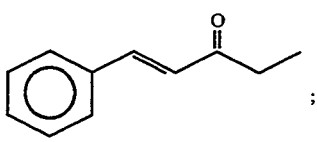;

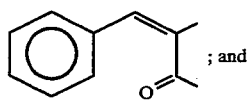; and

-continued

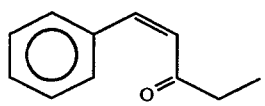

prepared according to Example I; 7.0 grams of a copper chromite catalyst and 65 grams of isopropyl alcohol.

The autoclave is sealed and hydrogen is fed into the autoclave while maintaining the temperature within the auto-clave at 180°–185° C. and while maintaining the pressure within the autoclave at 500 psig.

The hydrogenation is carried out over a period of eight hours.

At the end of the eight hour period the autoclave is cooled and opened and the contents are filtered.

The resulting filtrate is then fractionally distilled on a fractional distillation column yielding the following fractions:

| Fraction No. | Vapor Temp. (°C.) | Liquid Temp. (°C.) | Vacuum mm/Hg. Pressure |
|---|---|---|---|
| 1 | 23/28 | 23/105 | 12.0/3.0 |
| 2 | 95 | 113 | 1.0 |
| 3 | 97 | 113 | 1.0 |
| 4 | 98 | 114 | 1.0 |
| 5 | 98 | 115 | 1.0 |
| 6 | 98 | 115 | 1.0 |
| 7 | 97 | 115 | 1.0 |
| 8 | 98 | 116 | 1.0 |
| 9 | 98 | 115 | 1.0 |
| 10 | 97 | 115 | 1.0 |
| 11 | 97 | 115 | 1.0 |
| 12 | 97 | 115 | 1.0 |
| 13 | 98 | 115 | 1.0 |
| 14 | 98 | 115 | 1.0 |
| 15 | 98 | 115 | 1.0 |
| 16 | 99 | 175 | 1.0 |
| 17 | 29 | 210 | 0.5. |

Fractions 6–16 are bulked.

The resulting bulked fractions contain the compounds having the structures:

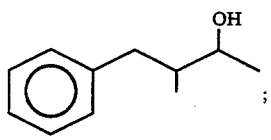;

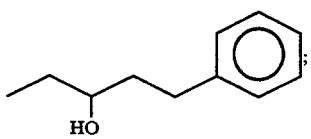;

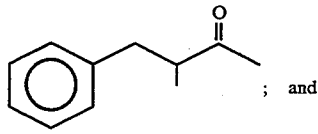; and

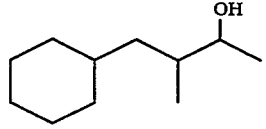

as confirmed by GLC, IR, NMR and mass spectral analysis.

The resulting product has an intense and long-lasting "wet floral", muguet, rose, green, lilac and ozoney aroma with natural green, floral, muguet and rose topnotes.

EXAMPLE III

The following Chypre formulation is prepared:

| Ingredients | Parts by Weight |
| --- | --- |
| Musk ambrette | 40 |
| Musk ketone | 60 |
| Coumarin | 30 |
| Oil of bergamot | 150 |
| Oil of lemon | 100 |
| Methyl ionone | 50 |
| Hexyl cinnamic aldehyde | 100 |
| Hydroxy citronellal | 100 |
| Oil of lavender | 50 |
| Texas cedarwood oil | 85 |
| Virginia cedarwood oil | 30 |
| Oil of sandalwood (East Indies) | 40 |
| Eugenol | 10 |
| Benzyl acetate | 30 |
| Alpha-Phenyl ethyl alcohol | 40 |
| Beta-Phenyl ethyl alcohol | 30 |
| Oakmoss absolute | 30 |
| Vetiver oil Venezuela | 25 |
| The mixture of compounds having the structures: prepared according to Example II, bulked distillation Fractions 6–16. | |

The mixture of compounds having the structures

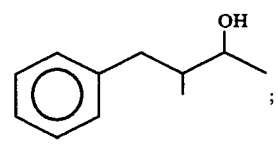

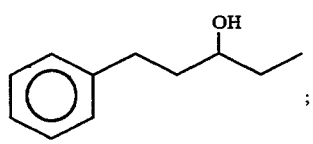

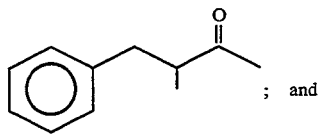

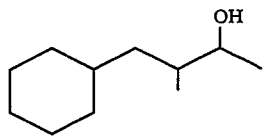

prepared according to Example II, bulked distillation Fractions 6-16 imparts to this Chypre formulation "wet floral", muguet, rose, green, lilac and ozoney undertones with natural green, floral, muguet and rose topnotes. Accordingly, the fragrance formulation of Example III can be described as "a Chypre aroma with "wet floral", muguet, rose, green, lilac and ozoney undertones and with natural green, floral, muguet and rose topnotes".

EXAMPLE IV

PREPARATION OF COSMETIC POWDER COMPOSITIONS

Cosmetic powder compositions are prepared by mixing in a ball mill 100 grams of talcum powder with 0.25 grams of each of the substances set forth in Table I below. Each of the cosmetic powder compositions has an excellent atom as described in Table I below.

TABLE I

| Substance | Aroma Description |
| --- | --- |
| The mixture of compounds having the structures: prepared according to Example II, bulked distillation Fractions 6-16. | An intense and long-lasting "wet floral", muguet, rose, green, lilac and ozoney aroma with natural green, floral, muguet and rose topnotes. |
| Perfume composition of Example III. | A Chypre aroma with "wet floral", muguet, rose, green, lilac and ozoney undertones and with natural green, floral, muguet and rose topnotes |

EXAMPLE V

PERFUMED LIQUID DETERGENTS

Concentrated liquid detergents (Lysine salt of n-dodecyl-benzene sulfonic acid as more specifically described in U.S. Pat. No. 3,948,818 issued on Apr. 6, 1976) with aroma nuances as set forth in Table I of Example IV are prepared containing 0.10%, 0.15%, 0.20%, 0.25%, 0.30% and 0.35% of the substance set forth in Table I of Example IV They are prepared by adding and homogeneously mixing the appropriate quantity of substance set forth in Table I of Example IV in the liquid detergent. The detergents all possess excellent aromas as set forth in Table I of Example IV, the intensity increasing with greater concentration of substance as set forth in Table I of Example IV.

EXAMPLE VI

PREPARATION OF COLOGNES AND HANDKERCHIEF PERFUMES

Compositions as set forth in Table I of Example IV are incorporated into colognes at concentrations of 2.0%, 2.5%, 3.0%, 3.5%, 4.0%, 4.5% and 5.0% in 80%, 85%, 90% and 95% aqueous food grade ethanol solutions; and into handkerchief perfumes at concentrations of 15%, 20%, 25% and 30% (in 80%, 85%, 90% and 95% aqueous food grade ethanol solutions). Distinctive and definitive fragrances as set forth in Table I of Example IV are imparted to the colognes and to the handkerchief perfumes at all levels indicated.

EXAMPLE VII

PREPARATION OF SOAP COMPOSITIONS

One hundred grams of soap chips [per sample]- (IVORY ®, produced by the Procter & Gamble Company of Cincinnati, Ohio), are each mixed with one gram samples of substances as set forth in Table I of Example IV until homogeneous compositions are obtained. In each of the cases, the homogeneous compositions are heated under 8 atmospheres pressure an 180° C. for a period of three hours and the resulting liquids are placed into soap molds. The resulting soap cakes, on cooling, manifest aromas as set forth in Table I of Example IV.

EXAMPLE VIII

PREPARATION OF SOLID DETERGENT COMPOSITIONS

Detergents are prepared using the following ingredients according to Example I of Canadian Pat. No. 1,007,948:

| Ingredient | Percent by Weight |
| --- | --- |
| "NEODOL ® 45-11 (a $C_{14}$-$C_{15}$ alcohol ethoxylated with 11 moles of ethylene oxide | 12 |
| Sodium carbonate | 55 |
| Sodium citrate | 20 |
| Sodium sulfate, water brighteners | q.s. |

This detergent is a phosphate-free detergent. Samples of 100 grams each of this detergent are admixed with 0.10, 0.15, 0.20 and 0.25 grams of each of the substances as set forth in Table I of Example IV. Each of the detergent samples has an excellent aroma as indicated in Table I of Example IV.

EXAMPLE IX

Utilizing the procedure of Example I at column 15 of U.S. Pat. No. 3,632,396, non-woven cloth substrates useful as drier-added fabric softening articles of manufacture are prepared wherein the substrate, the substrate coating and the outer coating and the perfuming material are as follows:

1. a water "dissolvable" paper ("Dissolvo Paper");
2. Adogen 448 (m.p. about 140° F.) as the substrate coating; and
3. an outer coating having the following formulation (m.p. about 150° F.):
   57%—$C_{20-22}$HAPS
   22%—isopropyl alcohol
   20%—antistatic agent
   1%—of one of the substances as set forth in Table I of Example IV.

Fabric softening compositions prepared according to Example I at column 15 of U.S. Pat. No. 3,632,396 having aroma characteristics as set forth in Table I of Example IV, consist of a substrate coating having a weight of about 3 grams per 100 square inches of substrate; a first coating on the substrate coating consisting of about 1.85 grams per 100 square inches of substrate; and an outer coating coated on the first coating consisting of about 1.4 grams per 100 square inches of substrate. One of the substances of Table I of Example IV is admixed in each case with the outer coating mixture, thereby providing a total aromatized outer coating weight ratio to substrate of about 0.5:1 by weight of the substrate. The aroma characteristics are imparted in a pleasant manner to the headspace in a dryer on operation thereof in each case using said drier-added fabric softener non-woven fabrics and these aroma characteristics are described in Table I of Example IV.

EXAMPLE X

HAIR SPRAY FORMULATIONS

The following hair spray formulation is prepared by first dissolving PVP/VA E-735 copolymer manufactured by the GAF Corporation of 140 West 51st Street, New York, N.Y. in 91.62 grams of 95% food grade ethanol, 8.0 grams of the polymer is dissolved in the alcohol. The following ingredients are added to the PVP/VA alcoholic solution.

| Ingredients | Weight Percent |
| --- | --- |
| Dioctyl sebacate | 0.05 |
| Benzyl alcohol | 0.10 |
| Dow Corning 473 fluid (prepared by the Dow Corning corporation) | 0.10 |
| Tween 20 surfactant (prepared by ICI America Corporation) | 0.10 |
| One of the perfumery substances as set forth in Table I of Example IV | 0.10 |

The perfuming substances as set forth in Table I of Example IV add aroma characteristics as set forth in Table I of Example IV which are rather intense and aesthetically pleasing to the users of the soft-feel, good-hold pump hair sprays.

EXAMPLE XI

CONDITIONING SHAMPOOS

Monamid CMA (prepared by the Mona Industries Company)(3.0 weight percent) is melted with 2.0 weight percent coconut fatty acid (prepared by Procter & Gamble Company of Cincinnati, Ohio); 1.0 weight percent ethylene glycol distearate (prepared by the Armak Corporation) and triethanolamine (a product of Union Carbide Corporation)(1.4 weight percent). The resulting melt is admixed with Stepanol WAT produced by the Stepan Chemical Company (35.0 weight percent). The resulting mixture is heated to 60° C. and mixed until a clear solution is obtained (at 60° C.).

GAFQUAT ® polymer (manufactured by GAF Corporation of 140 West 51st Street, New York, N.Y.)(5.0 weight percent) is admixed with 0.1 weight percent sodium sulfite and 1.4 weight percent polyethylene glycol 6000 distearate produced by Armak Corporation.

The resulting material is then mixed and cooled at 45° C. and 0.3 weight percent of perfuming substance as set forth in Table I of Example IV is added to the mixture. The resulting mixture is cooled to 40° C. and blending is carried out for an additional one hour in each case. At the end of this blending period, the resulting material has a pleasant fragrance as indicated in Table I of Example IV.

What is claimed is:

1. A process for forming phenyl- and cyclohexyl-substituted oxybutane derivative-containing mixtures comprising the steps of:

(1) first reacting methyl ethyl ketone with benzaldehyde in the presence of a sulfonic acid catalyst at a temperature of from about 20° C. up to about 90° C. for a period of time of from about one hour up to about six hours with the mole ratio of methyl ethyl ketone:benzaldehyde reactants being from about 1:1 up to about 3:1 and with the moles sulfonic acid per mole benzaldehyde being from about 0.1 up to about 0.4 according to the reaction:

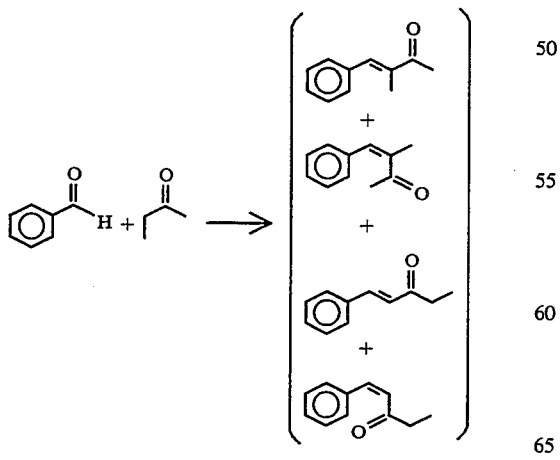

thereby forming a first mixture of phenyl pentenone derivatives having the structures:

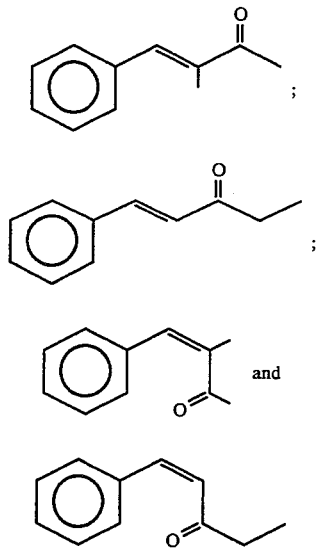

with the ratio of the compounds having the structures:

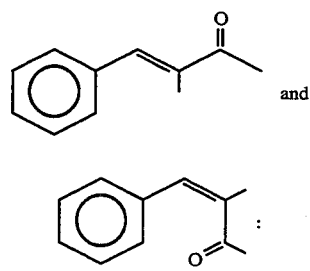

the compounds having the structures:

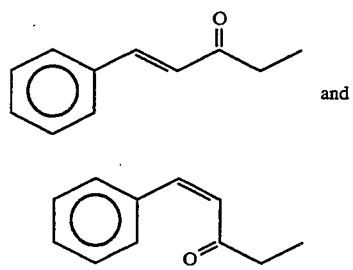

being from about 88:12 to about 95:5 and the ratios of the compound having the structure:

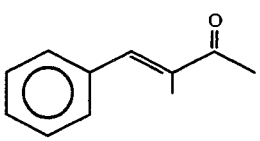

to the compound having the structure:

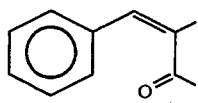

and the ratio of the compound having the structure:

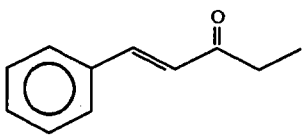

the compound having the structure:

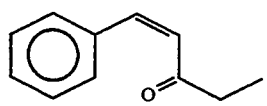

being 98:2; and then (2) reacting said first mixture of phenyl pentenone derivatives with hydrogen at a temperature of from about 150° C. up to about 200° C.; at a pressure of from about 250 psig up to about 600 psig for a period of time of from about one hour up to about ten hours in the presence of a catalyst selected from the group consisting of:
  (a) Raney nickel; and
  (b) copper chromite
according to the reaction:

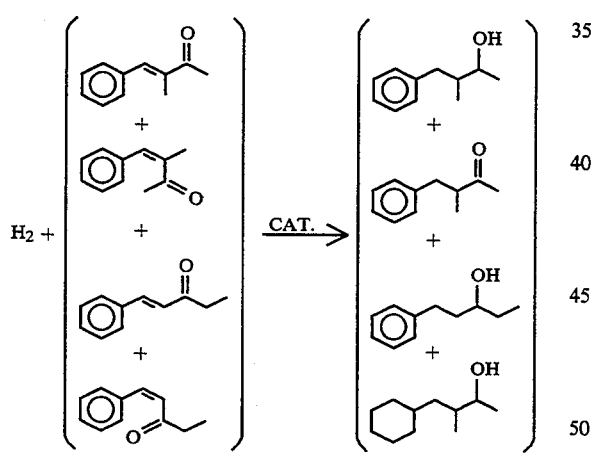

whereby a second mixture of phenyl- and cyclohexyl-substituted oxybutane derivative-containing mixture is formed containing:

from about 80 up to about 95% by weight of the compound having the structure:

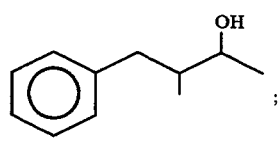

from about 4 up to about 12 weight percent of the compound having the structure:

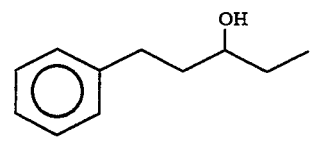

from about 1 up to about 5 weight percent of the compound having the structure:

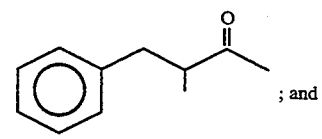

from about 1 up to about 5 weight percent of the compound having the structure:

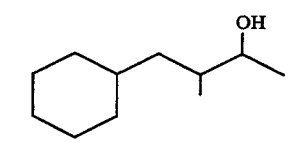

2. The process of claim 1 wherein in the reaction:

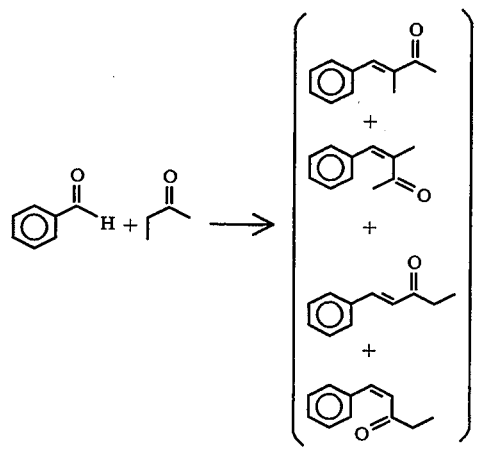

the sulfonic acid is 90% sulfuric acid and the reaction is run at 60° C.; and in the reaction:

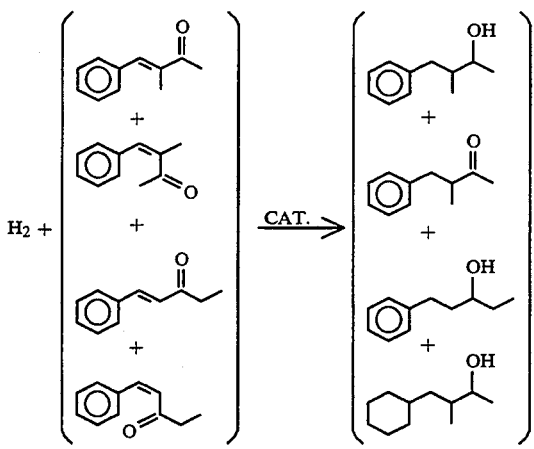

the hydrogenation catalyst is a copper chromite catalyst.

3. The product produced according to the process of claim 1.

4. The product produced according to the process of claim 2.

5. A mixture of compounds containing from about 80 up to about 95% by weight of the compound having the structure:

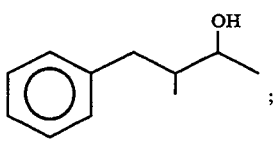

from about 4 up to about 12% by weight of the compound having the structure:

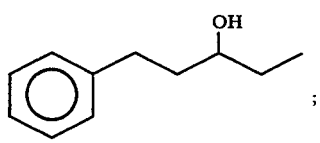

from about 1 up to about 5 weight percent of the compound having the structure:

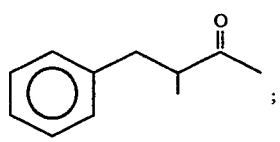

and from about 1 up to about 5 weight percent of the compound having the structure:

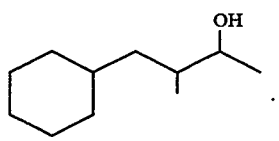

6. A process for augmenting, enhancing or imparting an aroma to or in a perfume composition, a cologne or a perfume article comprising the step of intimately admixing with a perfume composition, a cologne or a perfumed article, an aroma augmenting, enhancing or imparting quantity of the composition of matter defined according to claim 3.

7. A process for augmenting, enhancing or imparting an aroma to or in a perfume composition, a cologne or a perfumed article comprising the step of intimately admixing with a perfume composition, a cologne or a perfumed article, an aroma augmenting, enhancing or imparting quantity of the composition of matter defined according to claim 4.

8. A process for augmenting, enhancing or imparting an aroma to or in a perfume composition, a cologne or a perfumed article comprising the step of intimately admixing with a perfume composition, a cologne or a perfumed article, an aroma augmenting, enhancing or imparting quantity of the composition of matter defined according to claim 5.

9. A perfume composition comprising a perfume base and intimately admixed therewith an aroma augmenting, enhancing or imparting quantity of a composition of matter defined according to claim 3.

10. A perfume composition comprising a perfume base and intimately admixed therewith an aroma augmenting, enhancing or imparting quantity of a composition of matter defined according to claim 4.

11. A perfume composition comprising a perfume base and intimately admixed therewith an aroma augmenting, enhancing or imparting quantity of a composition of matter defined according to claim 5.

12. A perfumed article comprising a perfumed article base and intimately admixed therewith, an aroma augmenting, enhancing or imparting quantity of a composition of manner defined according to claim 3.

13. A perfumed article comprising a perfumed article base and intimately admixed therewith, an aroma augmenting, enhancing or imparting quantity of a composition of matter defined according to claim 4.

14. A perfumed article comprising a perfumed article base and intimately admixed therewith, an aroma augmenting, enhancing or imparting quantity of a composition of matter defined according to claim 5.

15. A cologne comprising ethyl alcohol, water and an aroma imparting quantity of a composition of matter defined according to claim 3.

16. A cologne comprising ethyl alcohol, water and an aroma imparting quantity of a composition of matter defined according to claim 4.

17. A cologne comprising ethyl alcohol, water and an aroma imparting quantity of a composition of matter defined according to claim 5.

18. A perfumed polymer comprising a microporous polymer and contained in the interstices thereof an aroma imparting quantity of a composition of matter defined according to claim 3.

19. A perfumed polymer comprising a microporous polymer and contained in the interstices thereof an aroma imparting quantity of a composition of matter defined according to claim 4.

20. A perfumed polymer comprising a microporous polymer and contained in the interstices thereof an aroma imparting quantity of a composition of matter defined according to claim 5.

* * * * *